United States Patent [19]

Dubrul

[11] Patent Number: 5,944,701
[45] Date of Patent: Aug. 31, 1999

[54] SELF COILING CATHETER

[76] Inventor: William R. Dubrul, No. 1 Uccelli Blvd., Redwood City, Calif. 94063

[21] Appl. No.: 08/942,588

[22] Filed: Oct. 2, 1997

Related U.S. Application Data

[60] Provisional application No. 60/027,591, Oct. 3, 1996.

[51] Int. Cl.⁶ .................................................. A61M 25/00
[52] U.S. Cl. ........................ 604/264; 604/280; 600/585
[58] Field of Search ..................................... 604/280, 264, 604/281, 282, 164–166, 272–274; 600/585; 606/116, 108, 180

[56] References Cited

U.S. PATENT DOCUMENTS

| | | | |
|---|---|---|---|
| 4,950,258 | 8/1990 | Kawai et al. | 604/281 |
| 5,211,183 | 5/1993 | Wilson | 128/772 |
| 5,221,269 | 6/1993 | Miller et al. | 604/281 |
| 5,666,968 | 9/1997 | Imran et al. | 128/772 |
| 5,709,874 | 1/1998 | Hanson et al. | 904/281 |
| 5,795,318 | 8/1998 | Wang et al. | 604/8 |

OTHER PUBLICATIONS

Flexmedics Corporation, Nitinol . . . The Material of Choice for Safer, More Effective Medical Procedures, Copyright 1989, 2 pages.

*Primary Examiner*—Manuel Mendez

[57] ABSTRACT

Medical guidewires have coiled proximal ends which allow and facilitate management of guidewires during use in an operating room.

15 Claims, 1 Drawing Sheet

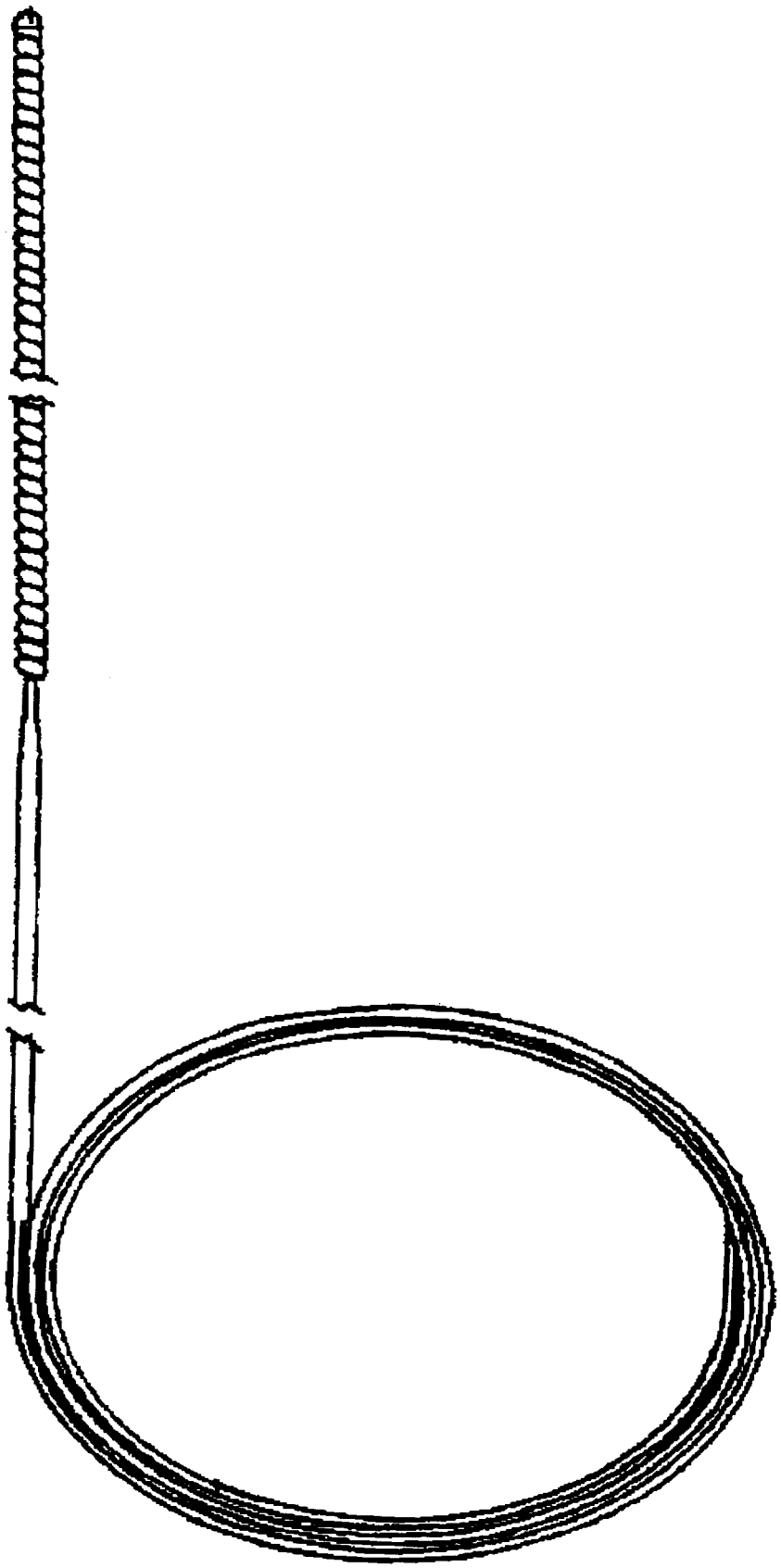
FIG.—1

_5,944,701_

SELF COILING CATHETER

The present application is a continuation-in-part of provisional Application No. 60/027,591, filed Oct. 3, 1996, the full disclosure of which is incorporated herein by reference.

BACKGROUND OF THE INVENTION

1. Field of the Invention

The present invention relates to medical devices and methods. In particular, the present invention relates to an improved catheters and guidewires and method for their use, where the device self-coiling over at least a portion of its proximal end.

Guidewire management in the operating room is problematic. Because of their length and high flexibility, it is usually necessary for an assistant to the physician to hold the proximal end of the guidewire while it is being introduced or withdrawn from the patient. Often, the assistant attempts to manually coil the guidewire in order to contain it and prevent it from falling to the floor or otherwise becoming contaminated (in which case the guidewire must be discarded and replaced). The assistant is not always successful.

For these reasons, it would be desirable to provide improved guidewires and methods for their use which facilitate manipulation and sterile maintenance of the guidewire in the operating room.

2. Description of the Background Art

Pertinent guidewire descriptions are set forth in a number of issued U.S. patents, including U.S. Pat. Nos. 5,411,476; 5,211,183; 4,984,581. A guidewire having a coiled extension is described in WO 96/29001. Guidewire feeding devices are described in U.S. Pat. Nos. 5,507,300; 5,366,444; and 5,124,416. A coiled feeding device for feeding a guidewire through the nose and esophagus into the duodenum is described in U.S. Pat. No. 4,631,054. A pin vise for helping grip the proximal end of a guidewire is illustrated in U.S. Pat. No. 4,858,810.

SUMMARY OF THE INVENTION

The present invention provides improved guidewires and catheters of the type having an elongate flexible body with a proximal end and a distal end. The improvement comprises configuring at least a proximal portion of the flexible body so that it will assume a coiled shape when unconstrained, e.g. when outside the body lumen to which it is to be introduced. In this way, the guidewire or catheter can be introduced from its coiled configuration into the body lumen in a conventional manner. That portion of the guidewire outside of the patient, however, will remain coiled so that manipulation and management of the proximal end is substantially facilitated. Once inside the body lumen, e.g. a blood vessel, the flexible body of the guidewire will have sufficient column strength and flexibility so that it can be guided through branches and tortuous regions of the target body lumen.

Often, the entire length of the flexible body will be coiled, in which case the guidewire or catheter can be packaged without using a packaging loop as is the present conventional practice. In other cases, however, it may be desirable to coil only a portion of the flexible body e.g. the proximal-most 50%, 60%, 75% or 95% of the length of the core in order to provide for improved management with minimal impact on the distal end which is most important to the guiding capability of the guidewire. The portion of the guidewire or catheter which is coiled will typically have a coil diameter in the range from 5 cm to 50 cm, usually from 10 cm to 20 cm. The flexible body may be composed of any conventional guidewire material, such as stainless steel, shape memory alloys, such as nickel-titanium alloys (available commercially under the tradename Nitinol™), and the like. Catheters may be formed from similar materials, where the material may be formed into a tube or may be used as reinforcement for a polymeric body.

In the case of shape memory alloys, the flexible body of the guidewire or catheter may be "programmed" to assume the desired coiled configuration at room temperature and to revert to a "memorized", usually straight configuration when introduced to the target body lumen at body temperature. Such programming is achieved by thermal treatment of the shape memory alloy in a conventional manner. Such techniques are described in more detail below. It will be appreciated that all or a portion of the flexible body of the guidewire may be thermally treated to impart the desired shape memory characteristics and coil or straighten configurations.

In other respects, the guidewires and catheters of the present invention may have the geometries, characteristics, and dimensions of those commonly employed for the intended purpose, e.g. introduction to a blood vessel. Typically, for vascular applications, the flexible body will have a length in the range from 50 cm to 200 cm and diameter in the range from 0.1 mm to 1 mm in the case of guidewires and diameter in the range from 0.5 mm to 5 mm in the case of tubular catheters.

A preferred guidewire of the present invention comprises a flexible body having a proximal end and a distal end. At least a portion of the flexible body is responsive to temperature so that it assumes or remains in a coiled configuration at room temperature, i.e. below 30° C., usually below 25° C., and straightens at body temperature, i.e. 37° C. The body will comprise a shape memory alloy, typically Nitinol™, and may be in a malleable condition when initially at room temperature and/or when returning to room temperature after transition to the martinsitic state at body temperature.

BRIEF DESCRIPTION OF THE DRAWINGS

FIG. 1 is a schematic illustration of a guidewire constructed in accordance with the principles of the present invention.

DESCRIPTION OF THE EXEMPLARY EMBODIMENTS

The guidewires and catheters of the present invention are used for intervention into the tubular channels (lumens) of the body (arteries, veins, biliary tract, urological tract, etc.) They are particularly convenient to use in an operating room environment because the self coil when outside the lumenal environment but straightened sufficiently when inside a body lumen so that they can be used as a guidewire. In a preferred aspect, the guidewires and catheters will have a flexible body composed of a shape memory alloy which has been programmed to coil at room temperature and to return to a straightened shape at body temperature as it enters the body. Upon removal from the body, it returns to its coiled shape. This unique coiling and uncoiling obviates the need for the user/interventionalist to either reinsert it into the packaging loop that comes with every guidewire or coil/ wrap in his/her hand as it is removed from the patient. A normal interventional guidewire can be 0.012" in diameter and as long as 60". This configuration allows for the "floppy" guidewire to easily become aseptic due to its contact outside the sterile field. Exemplary guidewire constructions are as follows:

Working Length
150 cm.

Working Diameter

The guidewire of the present invention has an outer diameter that ranges from 0.006" to 0.042" (0.15 mm to 1.07 mm), but can extend to smaller and larger sizes as technology and procedures require.

Physical Configuration

The guidewire of the present invention will have a predetermined shaped (probably circular in diameter of 6–10" (15 cm to 20 cm)) in the package, "as supplied" (at room temperature). It will usually become relaxed and straight guidewire at body temperature (37° C./98.6° F.). This relaxed condition means straight and floppy. The distal end will usually be tapered to a small distal diameter. This tapering will typically occur over the distal 6" (15 cm) of the device, but could occur over a greater length, and there may be more than one taper along its length. It will return to it's coiled configuration once removed from the body at room temperature (22.2° C./72° F.). Alternatively, it may return to a malleable condition once removed that would allow the interventionalist to "bunch it up" into any configuration desirable. Optionally, the guidewire may have a shaped tip or a tip that may be malleable so that it may be shaped by the user prior to introduction.

The guidewire of the present invention may have conventional lubricious coatings to enhance introduction into the target body lumen, e.g. hyaluronic or other equivalent coatings. As an advantage of the present invention, the guidewire need not be packaged in the usual packing loop, but instead can be placed in a sterile envelope or pouch, thus saving considerable packaging expense.

Guidewires formed from shape memory alloys may be shaped to have a straightened configuration at room temperature, with a coil configuration maintained by covering the body with a polymeric coating which constrains the guidewire or catheter in the coil. After introduction to the body lumen, i.e. raising the temperature to body temperature, the shape memory alloy would convert to the superelastic configuration (while still being in a straightened geometry), thus overcoming the coil force of the polymer coating.

The guidewires of the present invention could also be formed from known shape memory polymers, shape memory metal alloy coatings with a shape memory polymer, and/or electrical current could be used to effect the transition characteristics of the shape memory alloy of the guidewire. The flexible bodies may be formed from a single material, e.g. either shape memory alloy or stainless steel, or could be formed as composites or other variations thereof. Alternatively, a polymer could be included inside a hollow wire or (e.g. hypotube) or side-by-side extrusion. Further, the flexible core could be a shape memory alloy combined with stainless steel whereby no polymer is used.

An exemplary guidewire having a coiled proximal end is illustrated in FIG. 1. In this particular embodiment, a distal portion of the guidewire is not coiled and will thus retain the malleable or resilient characteristics typical of conventional guidewires. The proximal portion is coiled in a planar coil. As discussed above, however, a greater or lesser portion of the guidewire could be coiled, including the entire guidewire.

The flexible body may be fabricated by a technique known as two-way shaped memory (TWSM) or two-way shaped memory effect (TWME). Such techniques are described in detail in texts such as Duerig et al., *Engineering Aspects of Shape Memory Alloys*, Butterworth-Heinmann Ltd., 1990, Part III, pp. 195–206 and *The First International Conference on Shape Memory and Superelastic Technologies*, Mar. 7–10, 1994, Pelton et al., Eds., pp. 67–78. By employing such techniques, shape memory alloys, such as nickel-titanium alloy, may be programmed to change shapes simultaneously upon both heating and cooling. The guidewire body will have both a high temperature shape and a low temperature shape and may be cycled with a good degree of reproducability between the two shapes. This is accomplished by leaving some "reminders" of the deformed low temperature condition (stress-biased martinsite) in the high temperature phase in one of the following ways: (1) overdeformation while in the martinsitic condition; (2) shape memory cycling (cool-deform-heat, etc.); (3) pseudoelastic cycling (load-unload, etc.); (4) combined shape memory effect/pseudoelastic cycling; and (5) constrained temperature cycling of deformed martinsite.

Although the foregoing invention has been described in some detail by way of illustration and example, for purposes of clarity of understanding, it will be obvious that certain changes and modifications may be practiced within the scope of the appended claims.

What is claimed is:

1. An improved guidewire or catheter of the type having an elongated flexible body with a proximal end and a distal end, wherein the improvement comprises at least a portion of the flexible body being configured so that it assumes one configuration when unconstrained and at room temperature and another configuration when exposed to a different environment.

2. An improved guidewire or catheter as in claim 1, wherein the flexible body has a length in the range from 50 cm. to 200 cm. and a diameter in the range from 0.1 mm to 1 mm.

3. An improved guidewire or catheter as in claim 1, wherein at least the proximal 50% of the guidewire body is coiled.

4. An improved guidewire or catheter as in claim 1, wherein substantially the entire length of the flexible body is coiled.

5. An improved guidewire or catheter as in claim 1, wherein the coil has a diameter in the range from 5 cm to 50 cm.

6. An improved guidewire or catheter as in claim 1, wherein the flexible body is composed of a shape memory alloy which has the coiled configuration at room temperature and a straightened configuration at body temperature.

7. An improved guidewire or catheter as in claim 6, wherein the shape memory alloy comprises nickel-titanium alloy.

8. An improved guidewire or catheter as in claim 6, wherein the nickel-titanium has been programmed by TWSM or TWME.

9. An improved guidewire or catheter as in claim 1, wherein the flexible body is composed of a stainless steel alloy.

10. An improved guidewire or catheter as in claim 1, further comprising a polymeric coating, wherein the polymeric coating imparts the coil configuration.

11. An improved guidewire or catheter as in claim 1, wherein the flexible body is a shape memory alloy which is malleable at room temperature and straightens at body temperature.

12. An improved guidewire or catheter of the type having an elongated flexible body with a proximal end and a distal end, wherein the improvement comprises a temperature responsive body of at least a portion of which is one configuration at room temperature and another configuration at body temperature.

13. An improved guidewire or catheter as in claim 12, wherein the body becomes malleable after returning to room temperature from body temperature.

14. An improved guidewire or catheter as in claim 12, wherein the body is malleable at room temperature.

15. An improved guidewire or catheter as in claim 12, wherein the flexible body recoils after returning to room temperature from body temperature.

* * * * *